United States Patent [19]

Kawanabe et al.

[11] Patent Number: 4,808,269

[45] Date of Patent: Feb. 28, 1989

[54] METHOD FOR CONTROLLING AN OXYGEN CONCENTRATION SENSING DEVICE

[75] Inventors: Tomohiko Kawanabe; Masahiko Asakura; Noritaka Kushida; Hiroshi Hasebe, all of Wako; Tessho Yamada, Nagoya, all of Japan

[73] Assignees: Honda Giken Kogyo Kabushiki Kaisha, Tokyo; NGK Spark Plug Co., Ltd., Nagoya, both of Japan

[21] Appl. No.: 142,298

[22] Filed: Jan. 4, 1988

Related U.S. Application Data

[63] Continuation of Ser. No. 909,534, Sep. 22, 1986, abandoned.

[30] Foreign Application Priority Data

Sep. 30, 1985 [JP] Japan .................. 60-218501

[51] Int. Cl.$^4$ ............................................. G01N 27/46
[52] U.S. Cl. ...................... 204/1 T; 204/406; 204/425; 204/426
[58] Field of Search ................ 204/1 T, 1 S, 406, 421, 204/425, 426, 427

[56] References Cited

U.S. PATENT DOCUMENTS 4,707,241 11/1987 Nakagawa .................. 204/406

Primary Examiner—John F. Niebling
Assistant Examiner—Ben C. Hsing
Attorney, Agent, or Firm—Pollock, Vande Sande and Priddy

[57] ABSTRACT

A method of controlling an oxygen concentration sensor of the type having oxygen pump and sensor cell elements spaced from each other to form a gap or a restricted region both of which are to be placed in some gases containing an oxygen component, and a heater element for heating said oxygen pump and sensor cell elements under energization of a heater current supplied thereto.

A pump current is supplied to the oxygen pump element as long as the heater current is supplied to the heater element. However, the initiation of the supply of the pump current is somewhat delayed at the initial stage of the supply of the heater current in order to avoid incorrect operation due to the unstable cool state of the sensor, and to present possible flow of excessive pump current through the pump element which would cause deterioration of the oxygen pump element.

1 Claim, 4 Drawing Sheets

METHOD FOR CONTROLLING AN OXYGEN CONCENTRATION SENSING DEVICE

BACKGROUND OF THE INVENTION

Cross Reference To Related Applications

Oxygen concentration sensing devices whose structures are similar to the devices employed in the present invention are disclosed in Asakawa et al U.S. application Ser. No. 843,951 filed Mar. 25, 1986, for "Oxygen Concentration Sensing Device For an Air-Fuel Ratio Control System of an Automotive Internal Combustion Engine"; Kawanabe et al U.S. application Ser. No. 908,854 filed Sept. 18, 1986, for "Method for Controlling an Oxygen Concentration Sensor for Sensing an Oxygen Concentration in an Exhaust Gas of an Internal Combustion Engine"; and Kawanabe et al U.S. application Ser. No. 909,535 filed Sept. 22, 1986, for "Device for Sensing an Oxygen Concentration (etc.)"

This application is a continuation of Ser. No. 909,534, filed on Sep. 22. 1986, now abandoned.

Field of the Invention

The present invention relates to a method for controlling an oxygen concentration sensing device for sensing an oxygen concentration in gases such as the exhaust gases of an internal combustion engine.

Description of Background Information

Air/fuel ratio feedback control systems are becoming generally used for the fuel supply control of an internal combustion engine. In such systems the oxygen concentration in the exhaust gases of the engine is detected by an oxygen concentration sensor and an air/fuel ratio of the mixture to be supplied to the engine is feedback controlled in response to a result of the detection of the oxygen concentration for purification of the exhaust gases, improvement of the fuel economy, etc.

As an example of oxygen concentration sensor for use in the air/fuel ratio control system of the above mentioned type, there is an oxygen concentration sensor which produces an output signal whose level is proportional to the oxygen concentration in exhaust gases of the engine, examples of which are disclosed in U.S. Pat. No. 4,568,443 and Japanese Patent Application laid open No. 58-153155. This type of oxygen concentration sensor includes a sensor element whose general construction includes a pair of solid electrolyte members having oxygen-ion permeability. These oxygen-ion conductive solid electrolyte members are placed in the exhaust gases of the engine, and two pairs of electrodes are provided on the front and back surfaces of both of the solid electrolyte members. In other words, two pairs of electrodes respectively sandwich the solid electrolyte members. These two solid electrolyte members each cooperating with a pair of electrodes are arranged in parallel to each other, so as to face each other and to form a gap portion, or in other words, a restricted region between them for receiving therein gases containing an oxygen component.

With this arrangement, one of the solid electrolyte members serves as an oxygen pump element and the other one of the solid electrolyte members serves as a sensor cell element for sensing an oxygen concentration ratio. In the atmosphere of the exhaust gases, a drive current is supplied across the electrodes of the oxygen pump element in such a manner that one electrode facing the restricted region operates as a negative electrode. By the supply of this current, the oxygen component of the gas in the restricted region is ionized on the surface of the negative electrode of the oxygen pump element. The oxygen ions migrate through the inside of the oxygen pump element to the positive electrode, where the oxygen ions are released from the surface thereof in the form of the oxygen gas.

While this movement of oxygen ions is taking place, the oxygen concentration becomes different for the gas in the gap portion and the gas outside the electrodes of the sensor cell element because of a reduction of the oxygen gas component within the gap portion. Therefore a voltage appears across the electrodes of the solid electrolyte member operating as the sensor cell element whose magnitude should be regulated substantially linearly in proportion to the oxygen concentration of the test gas if the magnitude of the electric current supplied to the oxygen pump element, i.e., the pump current, is to be constant.

By means of this potential difference generated across the electrodes of the sensor cell element, it is determined whether the air/fuel ratio of the mixture supplied to the engine is rich or lean. If the air/fuel ratio control system is one in which the air/fuel ratio feed is controlled by the supply of air intake side secondary air, the secondary air is supplied when the air/fuel ratio is detected to be rich. On the other hand, the supply of the secondary air is stopped when the air/fuel ratio is detected to by lean, and the air/fuel ratio is controlled toward a target air/fuel ratio by the supply and stop of the air intake side secondary air.

In this type of oxygen concentration sensor, if an excessive pump current is supplied to the oxygen pump element, it causes the so called blackening phenomenon by which the oxygen ions are removed from the solid electrolyte member. For instance, when zirconium dioxide ($ZrO_2$) is utilized as the solid electrolyte, the oxygen ions $O_2$ are taken from the zirconium dioxide ($ZrO_2$) so that zirconium (Zr) is separated out. As a result of this balckening phenomenon, deterioration of the oxygen pump element takes place rapidly, to cause debasement of operation of the oxygen concentration sensor as a whole. It has been revealed that the pump current supplied to the oxygen pump element varies in terms of the voltages Vs appearing in the sensor cell element in accordance with variations of the oxygen concentration in the exhaust gases of the internal combustion engine as shown in linear solid lines in FIG. 1.

In this type of oxygen concentration sensor, it is necessary that the temperature of the sensor be sufficiently higher (for example, higher than 650° C.) than the exhaust gas temperature under a steady state operation, in order to obtain a proportional output signal characteristic of the sensor in which the sensor output signal varies substantially in proportion to the oxygen concentration. To meet this requirement, a heating device which is made up of a heater element is incorporated in the oxygen concedntration sensor and a drive current is supplied to the heater element at a time of the detection of the concentration so as to heat the heater element.

It is usual that the feed-back control for controlling the air/fuel ratio of the intake mixture in accordance with the output level of the oxygen concentration sensor ceases under conditions of the low engine temperature, the high load, the highland cruising, or the like. In such cases wherein the feedback control is OFF, it is required to stop the supply of the heater current to the heater element and of the pump current to the oxygen pump element. When, furthermore, the engine is stopped, the supply of the heater current is interrupted in order to avoid deterioration of the heater element. When, on the other hand, the feed-back control should be resumed, the heater current should be supplied to the heater element again and the pump current should be supplied to the oxygen pump element, thereby to restart the air/fuel ratio control in accordance with the magnitude of the pump current, that is, the output level of the oxygen concentration sensor device.

It is however, revealed that the oxygen concentration sensor needs some time periods after the heat current starts to flow through the heater element so as to operate correctly since the oxygen pump and sensor cell elements need some time period for their warming-up.

SUMMARY OF THE INVENTION

The primary object of the subject invention is to provide a method of controlling the oxygen concentration detecting device including an oxygen concentration sensor of the type having oxygen pump and sensor cell elements, while avoiding generation of an incorrect output signal from the sensor.

In order to achieve the above object there is provided a method of controlling an oxygen concentration detecting device including an oxygen concentration sensor having oxygen pump and sensor cell elements spaced from each other to form a restricted region, each of said elements being made of an oxygen-ion conductive solid electrolytic member and a pair of electrodes sandwiching said electrolytic member and heater elements for heating said oxygen pump and sensor cell elements under energization by a heater current supplied thereto, pump current supply means for supplying a pump current to said oxygen pump element in response to a pump current supply command while regulating the magnitude of said pump current so as to keep constant a sensor voltage appearing across the electrodes of said sensor cell element; and heater current supply means for supplying a heater current to said heater element in response to a heater current supply command, which features a first step of detecting the existence of said heater current supply command, a second step of detecting the lapse of a predetermined time period from the detection of the existence of said heater current supply command, and a third step of producing said pump current supply command upon the detection in said second step.

DETAILED DESCRIPTION OF EMBODIMENTS

Figure 1:
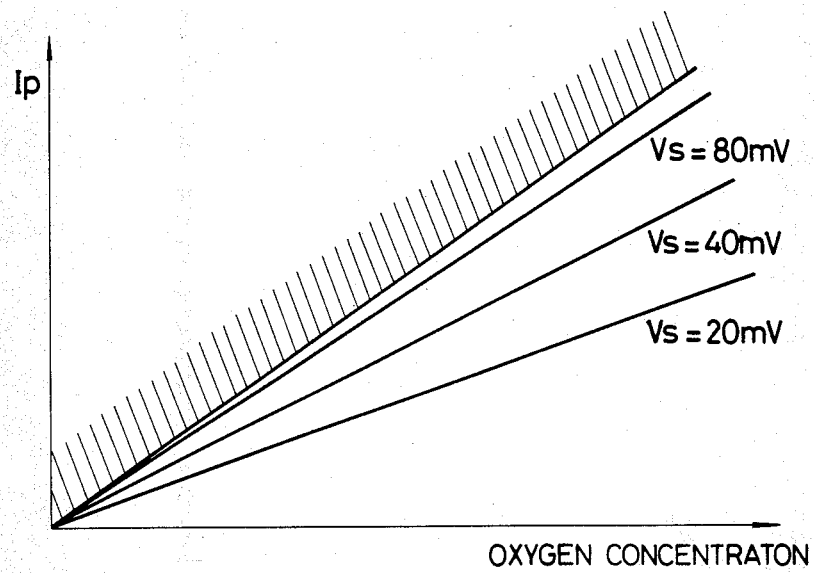
FIG. 1 is a graph showing typical relationships between the oxygen concentration in the exhaust gases of an internal combustion engine and the pump current of the oxygen concentration sensor having pump and sensor cell elements in terms of a voltage appearing in the sensor cell element.
Figure 2:
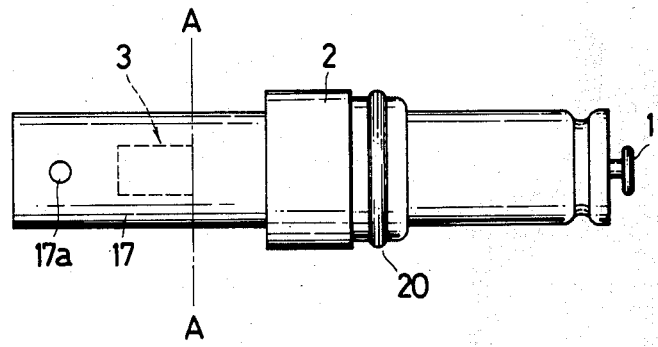
FIG. 2 is a side view of an oxygen concentration sensor of the type having oxygen pump and sensor cell element.

As shown in FIG. 2, a typical oxygen concentration sensor 20 producing an electric signal linearly varying in accordance with the oxygen concentration of a gas to be tested includes a housing 2 having a lead wire introducing hole 1 at an extremity thereof. At the other extremity of the housing 2, an oxygen concentration sensing part or element 3 is mounted. The oxygen concentration sensing element 3 is surrounded by a protection cover 17 which is formed into a cylinder and connected to the housing at an end portion thereof. The protection cover 17 is provided with a plurality of exhaust gas introduction holes 17a which are equally spaced about the circumference of the cover. Four exhaust gas introduction holes 17a are provided in this example. The part of the oxygen concentration sensor 20 illustrated on the left side of the line A—A of FIG. 2 is introduced into the exhaust manifold when the sensor 20 is mounted for operation.

Figure 3:
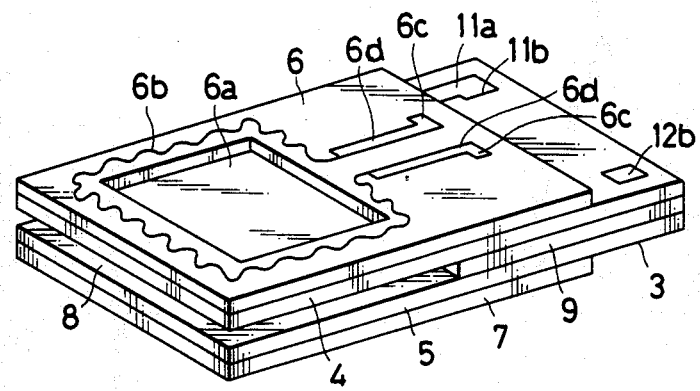
FIG. 3 is a perspective view of an oxygen concentration sensing part of the oxygen concentration sensor shown in FIG. 2.
Figure 4:
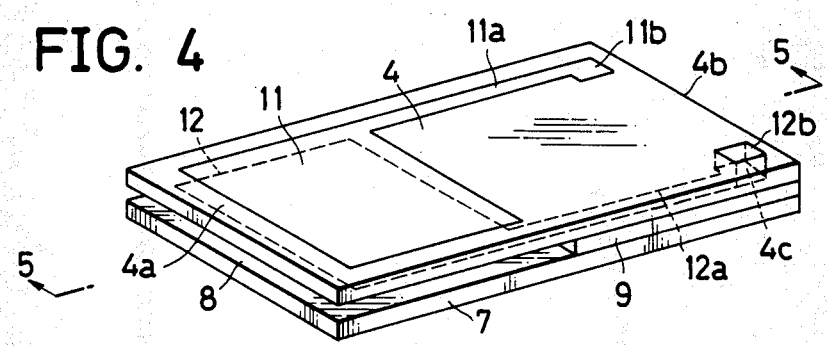
FIG. 4 is a perspective view corresponding to FIG. 3, showing a view of the oxygen pump and sensor cell elements from which heater elements shown in FIG. 3 are removed.
Figure 5:
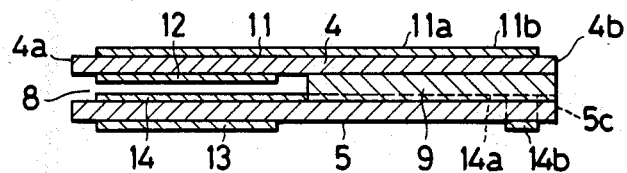
FIG. 5 is vertical cross-sectional view taken on the plane of the lines 5—5 of FIG. 4, ilustrating an internal construction of the oxygen concentration sensing part.

As illustrated in FIG. 3, the oxygen concentration detection element 3 comprises a pair of flat elongated elements 4 and 5 and a pair of flat heater elements 6 and 7 respectively provided on outer sides of the flat elongated elements 4 and 5. As clearly shown in FIGS. 4 and 5, the flat elongated elements 4 and 5 are arranged in parallel with each other, so that main surfaces of both elements 4 and 5 face each other. A gap portion 8 is formed between end portions of the flat elongated elements 4 and 5 which are connected together by means of a spacer 9 at the other end portions (second end portions) thereof. The gap portion 8 functions as a restricted region receiving therein a gas containing the oxygen. One of the flat elongated elements 4 and 5, (element 4) is an oxygen pump element whose main part is made of a sinter of an oxygen-ion conductive solid electrolytes. The oxygem pump element 4 is provided, at corresponding positions of both surfaces of an end portion 4a thereof a pair of square electrode layers 11 and 12 made of a porous heat resisting metal. One of the square electrode layers 11 and 12 (the electrode layer 11) is connected, at a corner thereof, to a lead wire 11a which is made of a heat resisting metal and linearly extends to the second end portion 4b of the oxygen pump element 4. Similarly, the other one of the square electrode layers 11 and 12 (the electrode layer 12) is connected, at a corner thereof which is away from the connection point between the square electrode layer 11 and the lead wire 11a, to a lead wire 12a also made of the heat resisting metal and linearly extending to the second end portion 4b of the oxygen pump element 4. The lead wire 12a is connected to a terminal part 12b located on the other side, after running through a though hole 4c which passes between the front and back faces of the oxygen pump element 4. The lead wire 11a is connected to a terminal part 11b also formed on the second end portion 4a. In short, the terminal parts 11b and 12b respectively of the lead wires 11a and 12a are provided on one of the main surfaces of the oxygen pump element 4.

The other one of the flat elongated element (the element 5) is a sensor cell element for sensing an oxygen concentration ratio, and is also made of the sinter of the oxygen-ion conductive solid electrolyte. This sensor cell element 5 is constructed in the same manner as the oxygen pump element 4, and is provided, on both of the front and back surfaces thereof, with square electrode layers 13 and 14, and lead wires 13a and 14a. Terminal parts 13b and 14b are provided on one of the main surfaces in which the electrode layer 13 is formed. In addition, the lead wire 14a and the terminal part 14b are connected to each other by means of a through hole 5c.

Typical examples of the above explained oxygen-ion conductive solid electrolyte member for the elements 4 and 5 are solid solutions of zirconia with yttria or calcia. However, other solid solutions of cerium dioxide, thorium dioxide, or hafnium dioxide may be also used. As the electrode layers 11 through 14, the lead wires 11a through 14a, the terminal parts 11b through 14b, platinium (Pt), Ruthenium(Ru), and Palladium (Pd) may be used. In production, the above mentioned metal is applied to form a coating by a suitable method such as flame spraying, chemical plating, or evaporation.

Next, the flat heater elements 6 and 7 illustrated in FIG. 3 will be explained.

The main bodies of the heater elements 6 and 7 are rectangular plates each made of an inorganic insulating material such as alumina or spinel. The lengthwise size of the heater elements 6 and 7 is slightly smaller than that of the flat elongated elements 4 and 5. At an end portion of the heater element 6, an opening portion 6a provided in registration is size and position with the electrode layer 11 on the oxygen pump element 4. The heater element 6 includes a wavelike heater wire 6b provided around the opening portion 6a. The heater wire 6b is electrically connected to a terminal parts 6c which are formed in the other end portion of the heater element 6, through lead wires 6d. The heater wires 6b, the terminal parts 6c, and the lead wires 6d are made of a heat resisting metal such as platinum (Pt). Although not illustrated in the drawings, the other heater element 7 is also provided with an opening, a heater wire (which will be denoted by 7b in the following description) and lead wires corresponding to those provided in to the heater element 6.

The oxygen concentration detection operation of the oxygen concentration sensor 20 having the above explained configuration will be discussed hereinafter.

A pump current is supplied across the electrode layers 11 and 12 of the oxygen pump element 4 from the pump current supply circuit 21 so that the electrode layer 11 which is located on the outer side of the oxygen pump element 4 operates as a positive electrode. By the supply of the pump current, oxygen ions migrate from the inner electrode layer 12 to the outer electrode layer 11 through the solid electrolyte member of the oxygen pump element 4. As a result, oxygen in the gap portion 8 between the oxygen pump element and the sensor cell element 5 is pumped toward the outside of the oxygen pump element.

When the oxygen is pumped out from the gap portion 8 as explained above, the oxygen concentration become different for the gas outside of the sensor cell element 5, i.e. there is a difference in oxygen concentration between the exhaust gas and the gas in the gap portion 8. By this difference the oxygen concentration, a voltage is generated across the electrode layers 13 and 14 of the sensor cell element 5. This voltage will reach a constant level when the amount of oxygen which flows into the gap portion 8 freely from the openings 17a of three directions and the amount of oxygen pumped out from the gap portion 8 by the operation of the oxygen pump element 4 have attained an equilibrium.

The voltage thus generated is supplied to the pump current supply circuit 21 (FIG. 6) by which a pump current value $I_p$ is varied so that the voltage generated across the electrodes of the sensor cell element 5 is maintained at a predetermined constant level. Therefore, under a condition of a constant temperature, the pump current value $I_p$ becomes proportional to the oxygen concentration in the exhaust gas.

Figure 6:
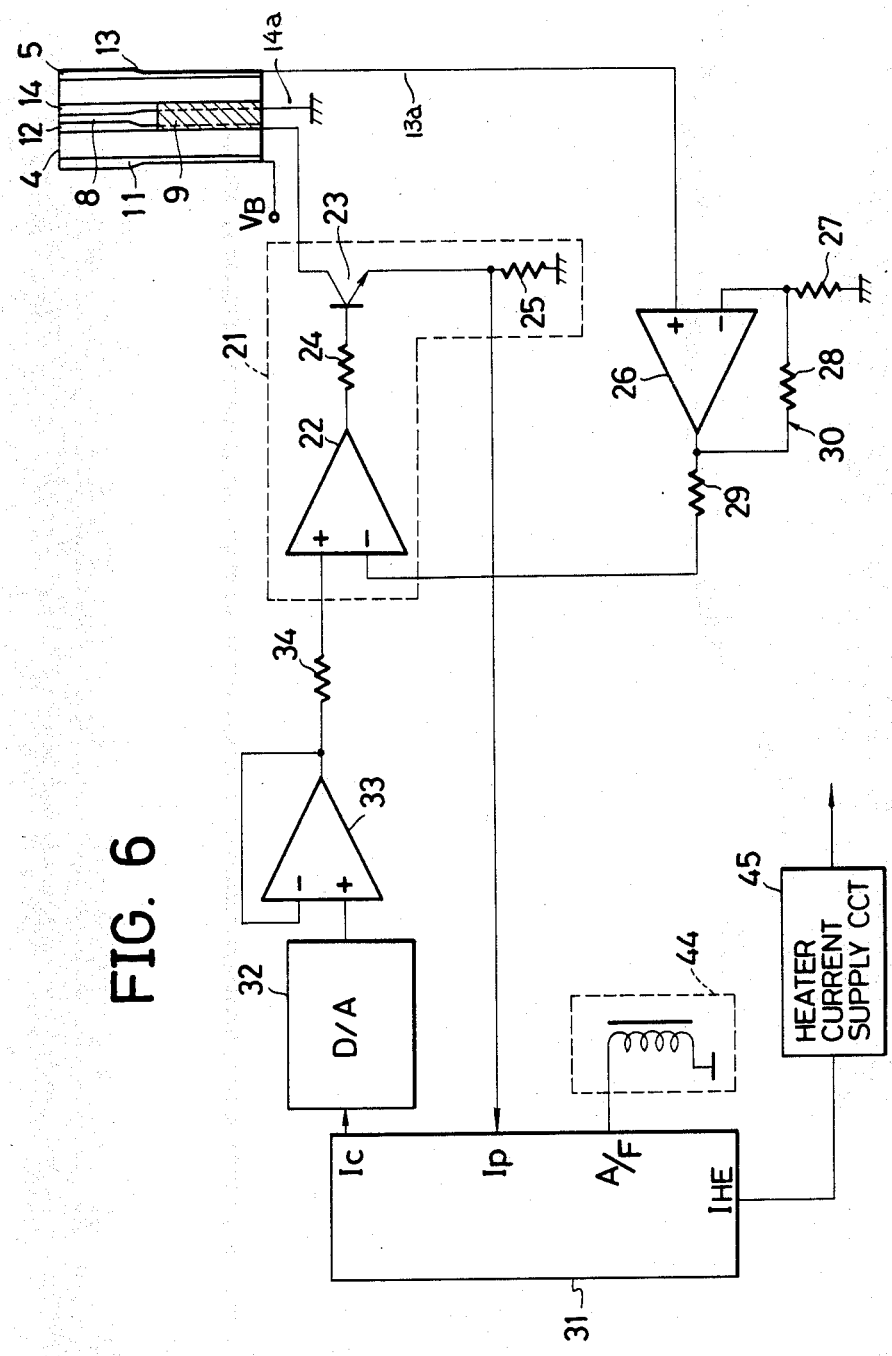
FIG. 6 is a circuit diagram of a air/fuel ratio control system using the oxygen concentration sensor of FIG. 2.

FIG. 6 shows an air/fuel ratio control apparatus for an internal combustion engine, which apparatus utilizes an oxygen concentration detection device according to the present invention. The oxygen concentration detection device comprises an oxygen concentration sensor having an oxygen pump element 4 for pumping oxygen gas into or out of a restricted region 8 into which any gases containing an oxygen component such as the exhaust gases are introduced. To the electrodes 11 and 12 of the pump element 4 is supplied a pump current from a current supply circuit 21. The current supply circuit 21 includes an operational amplifier 22 and an NPN transistor 23 having its base connected through a resistor 24 to the output terminal of the operational amplifier 22 and its emitter grounded through a resistor 25. The resistor 25 is provided for detecting the pump current $I_p$ flowing across the electrodes 11 and 12. A voltage appearing across the resistor 25 is supplied as a signal representing the pump current $I_p$ to an input terminal $I_p$ of control circuit 31. The collector of the transistor 23 is connected to the inner electrode 12 of the pump element 4 through a line 12a. The outer electrode 11 is connected through a line 11a to a source voltage $V_B$.

The oxygen concentration sensor includes a sensor cell element 5 facing the oxygen pump element 4 via the restricted region 8 for producing a voltage representative of the oxygen concentration within the restricted region in terms of the oxygen concentration outside of the restricted region 8. The inner electrode 14 of the sensor cell element 5 is connected through a line 14a to the ground. The outer electrode 13 of the sensor cell element 5 is connected through a line 13a to an non-inversion input terminal of an operational amplifier 26 which constitutes a non-inversion amplifier 30 in cooperation with resistors 27 through 29. The control circuit 31 has a control output terminal Ic to which an input terminal of a D/A converter 32 is connected. The D/A converter 32 produces a voltage representative of a command data DVs emitted from the control output terminal Ic of the control circuit 32. The D/A converter 32 has its output terminal connected to a non-inversion input terminal of an operational amplifier 33 functioning as a voltage follower, the output terminal of the operational amplifier 33 being in turn connected through a resistor 34 to a non-inversion input terminal of th operational amplifier 22.

The control circuit 31 may be constituted by a so-called microcomputer which has output terminals for A/F and $I_{HE}$ respectively producing an A/F control command signal and a heater current supply control signal. The A/F control command signal is applied to a secondary air regulator 44 including a solenoid valve provided at a secondary air supply passageway communicating with a portion of the intake air passageway downstream of the throttle valve of the internal combustion engine. The heater current supply control signal is supplied to a heater current circuit 45 which in turn supplies heater currents to the respective heating elements 6 and 7 when the heater current control signal commands the supply of the heater current. When the heater current supply control signal commands the interruption of the heater current then the heat current supply circuit 45 interrupts the heat currents flowing through the heating elements 6 and 7.

When, with the above-mentioned arrangement, the control circuit 31 produces the command data DVs through the output terminal Ic, the D/A converter 32 converts the command data DVs into a voltage which is applied to the voltage follower circuit 33. The output voltage from the voltage follower circuit 33 is applied through the resistor 34 to the non-inversion input terminal of the operational amplifier 22 as a reference voltage $V_{rl}$. When, at this instance, the voltage at the inversion input terminal of the operational amplifier 22 is lower than the reference voltage $V_{rl}$, the output level of the operational amplifier 22 becomes high so that the transistor 23 becomes conductive whereby the pump current flows across the electrode layers 11 and 12 of the oxygen pump element 4.

When the pump current flows, a voltage $V_s$ appears across the electrode layers 13 and 14 of the sensor cell elements 5. The voltage Vs is supplied to the non-inversion input terminal of amplifier 30. The non-inversion amplifier 30 amplifies the voltage $V_s$ into a voltage $V_s'$ which is supplied through the resistor 29 to the inversion input terminal of the operational amplifier 22. When the voltage $V_s$ rises, the output voltage $V_s'$ also rises, When the output voltage $V_s'$ exceeds the reference voltage $V_{rl}$, the output level of the operational amplifier 22 is inverted to a lower level so that the transistor 23 becomes non-conductive. Due to the non-conductive state of the transistor 23 the pump current decreases so that the voltage $V_s$ across the electrode layers 13 and 14 decreases thereby causing the voltage $V_s'$ to decrease. When the voltage $V_s'$ lowers below the reference voltage $V_{rl}$ then the output level of the operational amplifier 22 becomes high again so as to cause the pump current to increase. The above-mentioned sequence is repeated at a high frequency so that the voltage $V_s$ converges at a level according to the command data $DV_s$.

The magnitude of the pump current $I_p$ flowing across the electrode layers 11 and 12 of the element 4 is detected as a voltage $V_p$ appearing across the resistor 25 which is delivered to the input terminal $I_p$ of the control circuit 31. The control circuit 31 takes therein the voltage $V_p$ as a signal representing $I_p$ and then compares the value $I_p$ with a reference current $I_{rl}$ which corresponds to a target air/fuel ratio. When the value $I_p$ is smaller than the reference current $I_{rl}$, then the control circuit 31 determines that the air/fuel ratio of the intake air-fuel mixture supplied to the engine is rich and actuates the solenoid valve 44 to its open position so as to introduce the secondary air to the intake side of the engine. When, on the other hand, the value $I_p$ is larger than $I_{rl}$, then the control circuit 31 determines that the air/fuel ratio of the intake air-fuel mixture is lean and de-energizes the solenoid valve 44 to its closed position thereby to terminate the secondary air supply to the intake side of the engine.

Figure 7:
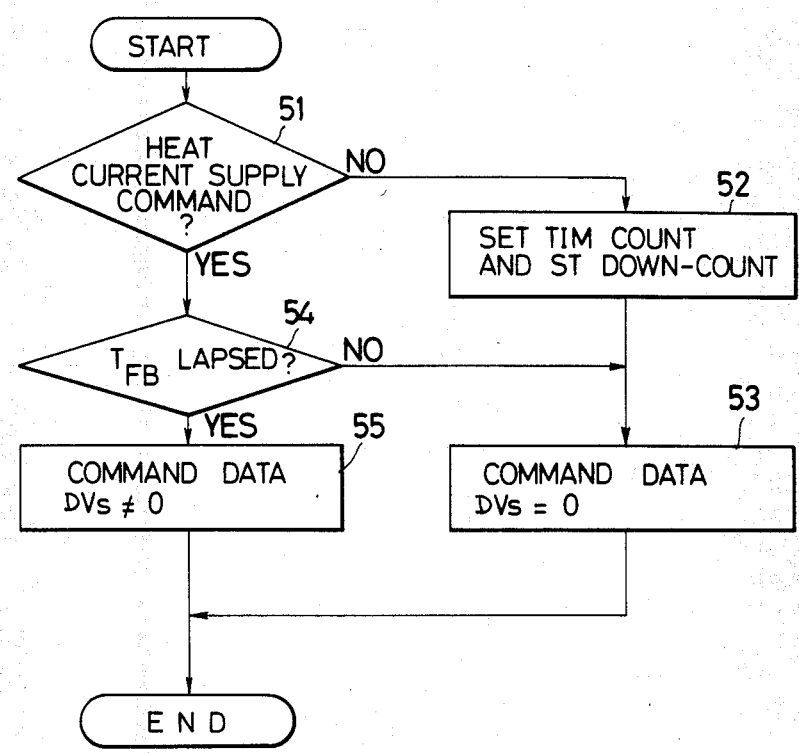
FIG. 7 is a flowchart showing steps of the control method according to the present invention performed by the system of FIG. 6.

The control circuit 31 is preferably constituted by a microprocessor operative in synchronism with operation of the engine or clock pulses. The control circuit 31 performs a re-start operation as shown by the flowchart of FIG. 7. When, on the other hand, the control circuit 31 determines that the air/fuel ratio feed-back control loop is to be closed again at, for example, the end of a highland cruising state of the engine, the control circuit 31 produces the heat current supply command to the current supply circuit 45 which in turn causes the heater current to flow though the heating elements 6 and 7. The re-start operation of the control circuit 31 is done in a sub-routine program which is started intermittently and firstly determines whether or not the heat current supply command is present at step 51. When the heat current supply command is not present an inner time counter A (not shown) incorporated in the control circuit 31 is set to a time count value $T_{FB}$, the inner time counter A being down counted, at a step 52. At the next step 53, the command data $DV_s$ is set to a value such as "0000" corresponding to a state $DV_s=0$ so as to cease the pump current. When the heat current supply command is found to exist at the step 51, a step 54 tests whether or not the down-count in the time, counter A is finished due to the lapse of a time period corresponding to the value $T_{FB}$. When it has been determined that the down-count has not been finished, then the command data $DV_s$ is kept at zero. When, to the contrary, the completion of the down count of the time counter A has been detected at the step 54, then the command data $DV_s$ is set to be a pertinent value which is not zero at a step 55.

Accordingly, it is now apparent that the pump current supply across the electrode layers 11 and 12 of the element 4 is initiated upon the lapse of a time period $T_{FB}$ from the start of the heater current supply to the heating elements 6 and 7 upon the closure of the feedback loop for air/fuel ratio control.

As is apparent from the foregoing description, the pump current supply to the oxygen pump element is initiated upon the lapse of a predetermined time period from the start of the heater current supply to the heating elements in the oxygen concentration detecting system according to the invention. In other words, the pump current supply is inhibited during the time that the oxygen pump element and the sensor cell element are cold i.e. below a predetermined temperature, thereby to avoid erroneous operation in the detection of the oxygen concentration upon the start of the heater current supply. Furthermore, too much pump current, which would cause the blackening phenomenon in the pump element, can be avoided due to the delayed start of the pump current from the start of the heat current supply, so that the life of the oxygen pump element can be prolonged according to the subject invention.

What is claimed is:

1. In a method of controlling an oxygen concentration detecting device including an oxygen concentration sensor having oxygen pump and sensor cell elements spaced from each other to form a restricted region between said elements, each of said elements being made of an oxygen-ion conductive solid electrolytic member and a pair of electrodes sandwiching said electrolytic member, said sensor including heater means for heating said oxygen pump and sensor cell elements under energization by a heater current supplied thereto, pump current supply means for supplying a pump current to said oxygen pump element in response to a pump current supply command while regulating the magnitude of said pump current so as to reduce deviations between a sensor voltage appearing across the electrodes of said sensor cell element and a reference voltage; detecting means for producing an oxygen concentration signal based on the magnitude of said pump current, said signal representing the oxygen concentration of an oxygen-containing gas introduced into said restricted region; and heat current supply means for supplying a heat current to said heater means in response to a heater current supply command, the improvement which comprises:

a first step of initiating the production of said heater current supply command while interrupting the supply of said pump current;

a second step of detecting the termination of a predetermined time period subsequent to the initiation of said heater current supply command; and a third step of initiating said pump current supply command only upon the termination of said predetermined time period detected in said second step to assure that no pump current is supplied to said oxygen pump element during said predetermined time period so as to cease production of said oxygen concentration signal during said predetermined period and to commence the production of said oxygen concentration signal upon the lapse of said predetermined time period whereby the detection of said oxygen concentration occurs only after said sensor voltage has achieved a constant value and said pump current is proportional to the oxygen concentration of the oxygen-containing gas introduced into said restricted region.

* * * * *